(12) United States Patent
Craig

(10) Patent No.: US 7,757,815 B2
(45) Date of Patent: Jul. 20, 2010

(54) METHOD AND APPARATUS FOR SAMPLING LUBRICANT

(75) Inventor: Terry Allen Craig, Greenup, KY (US)

(73) Assignee: General Electric Company, Schenectady, NY (US)

( * ) Notice: Subject to any disclaimer, the term of this patent is extended or adjusted under 35 U.S.C. 154(b) by 825 days.

(21) Appl. No.: 11/283,094

(22) Filed: Nov. 18, 2005

(65) Prior Publication Data

US 2007/0137935 A1 Jun. 21, 2007

(51) Int. Cl.
*F16N 39/00* (2006.01)
(52) U.S. Cl. ........................ 184/6.21; 184/6.12; 184/26; 210/232; 210/767; 123/196 R; 73/863
(58) Field of Classification Search ................ 184/6.21, 184/26, 6.12, 6.13; 73/61.71, 53.01, 53.05, 73/53.07, 61.42, 61.59, 61.61, 863.23, 863.25, 73/863.31, 863.33, 863.41, 866; 210/85, 210/96.1, 232, 416.5, 422, 435, 739, 767; 137/237, 240, 597; 422/68.1, 101
See application file for complete search history.

(56) References Cited

U.S. PATENT DOCUMENTS

| | | | |
|---|---|---|---|
| 3,307,567 A * | 3/1967 | Gogarty et al. | 137/13 |
| 5,139,673 A * | 8/1992 | Martin | 210/463 |
| 5,558,058 A | 9/1996 | Ming et al. | |
| 5,785,151 A | 7/1998 | Fry et al. | |
| 6,908,545 B2 | 6/2005 | Mouhebaty et al. | |
| 7,179,390 B1 * | 2/2007 | Layton | 210/767 |
| 2003/0062717 A1 * | 4/2003 | Thomas et al. | 285/18 |
| 2005/0118063 A1 * | 6/2005 | Kawabata et al. | 422/82.05 |
| 2006/0174960 A1 * | 8/2006 | Evans | 138/137 |

* cited by examiner

*Primary Examiner*—Robert A Siconolfi
*Assistant Examiner*—San Aung
(74) *Attorney, Agent, or Firm*—William Scott Andes, Esq.; Armstrong Teasdale LLP

(57) ABSTRACT

A method for sampling lubricant from a lubrication system including a pump for pumping lubricant between a reservoir and a sump. The method includes removing a filter from the pump, replacing the filter with a sampling device having a fluid passage, channeling lubricant returned from the sump to the pump into the fluid passage, and discharging lubricant from the pump by discharging lubricant from the fluid passage.

20 Claims, 7 Drawing Sheets

METHOD AND APPARATUS FOR SAMPLING LUBRICANT

BACKGROUND OF THE INVENTION

This invention relates generally to sampling lubricant, and more specifically, for example, to methods and apparatus for sampling lubricant from a gas turbine engine.

At least some known gas turbine engine lubrication pumps scavenge oil from separate sumps and re-merge the oil before returning it to a reservoir. Each of the separate sumps may include its own filter, such as a screen and/or magnet. However, at least some of such known filters may be inefficient. Accordingly, at least some known gas turbine engines include another scavenge filter that filters lubricant after it has been merged from the separate sumps. It may sometimes be desirable to sample lubricant from the engine to investigate any problems in the engine. However, because the lubricant may not be filtered by the scavenge filter until after being merged, it may be difficult to determine a source of any contamination and/or debris in the engine, such as abrasive contamination, magnetic debris, and/or non-magnetic debris. At least some known gas turbine engines are investigated by disconnecting lubricant lines from the lubrication pump and/or the lubrication reservoir and re-routing the lubricant to an external filtering and/or sampling device. However, such an investigation method may be time consuming and inefficient, which may increase a cycle time and/or cost of maintaining the gas turbine engine. Moreover, because the lubricant lines must be disconnected and thereafter reconnected after investigation, such investigation methods may facilitate causing lubricant to leak from such connections during operation of the engine.

BRIEF DESCRIPTION OF THE INVENTION

In one aspect, a method is provided for sampling lubricant from a lubrication system including a pump for pumping lubricant between a reservoir and a sump. The method includes removing a filter from the pump, replacing the filter with a sampling device having a fluid passage, channeling lubricant returned from the sump to the pump into the fluid passage, and discharging lubricant from the pump by discharging lubricant from the fluid passage.

In another aspect, a lubrication system includes a pump coupled in flow communication with a sump for pumping lubricant between the pump and the sump, and an external device that is external to the pump. The external device is configured to at least one of filter lubricant and analyze lubricant. The lubrication system also includes a sampling device coupled to the pump. The sampling device includes a fluid passage coupled in flow communication with the pump and with the external device. The fluid passage is configured to receive lubricant returned to the pump from the sump and configured to discharge lubricant into the external device.

DETAILED DESCRIPTION OF THE INVENTION

Figure 1:
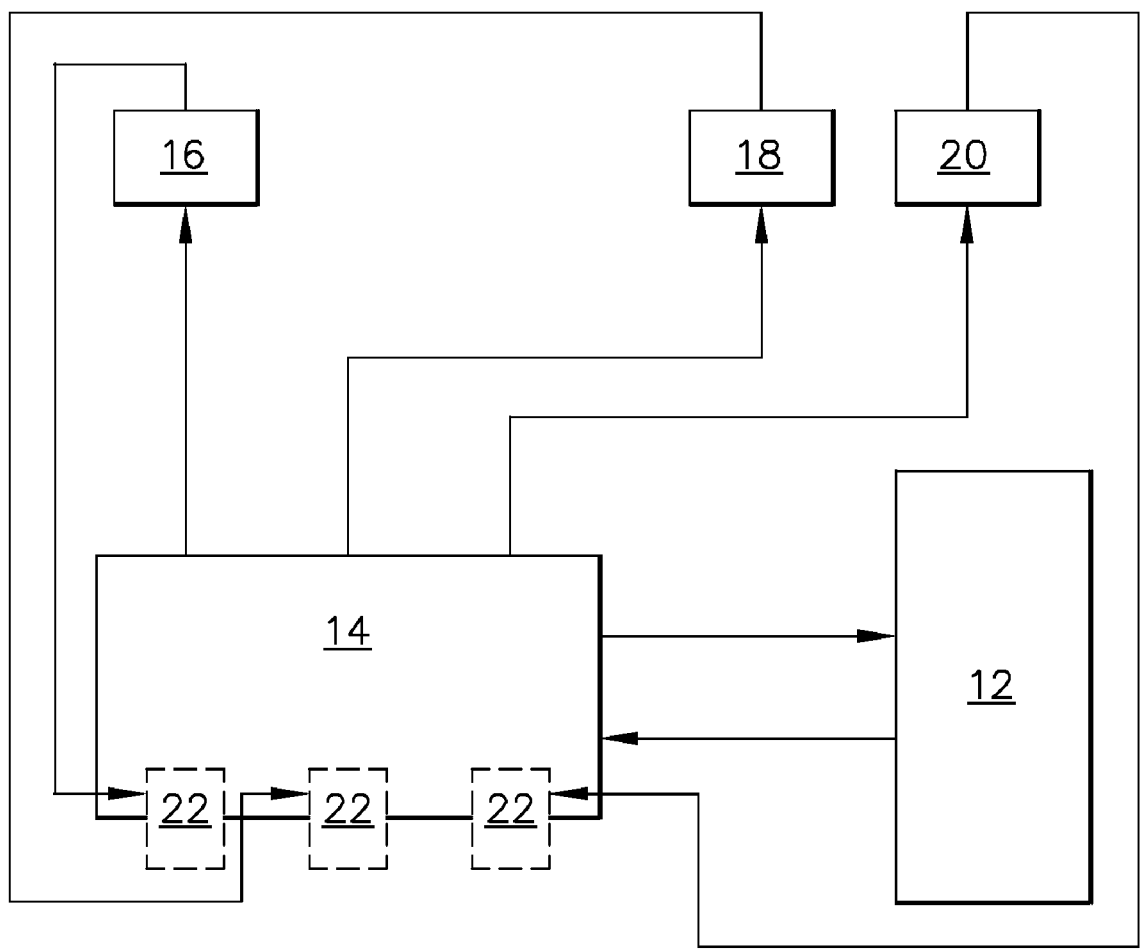
FIG. 1 is a block diagram of an exemplary lubrication system.

FIG. 1 is a schematic block diagram of an exemplary known lubrication system 10 for, for example, a gas turbine engine (not shown). System 10 includes a reservoir 12 for containing lubricant and a pump 14 for pumping lubricant between reservoir 12 and one or more sumps 16, 18, and 20 of the gas turbine engine. More specifically, pump 14 is coupled in flow communication with each sump 16, 18, and 20, and with reservoir 12. Although three sumps 16, 18, and 20 are described and illustrated, other known lubrication systems may pump lubricant to and/or from any number of sumps, including only one sump. Moreover, although system 10 includes reservoir 12, sometimes referred to as a "dry-sump" system, other known lubrication systems may not include reservoir 12, sometimes referred to as "wet-sump" systems.

Figure 2:
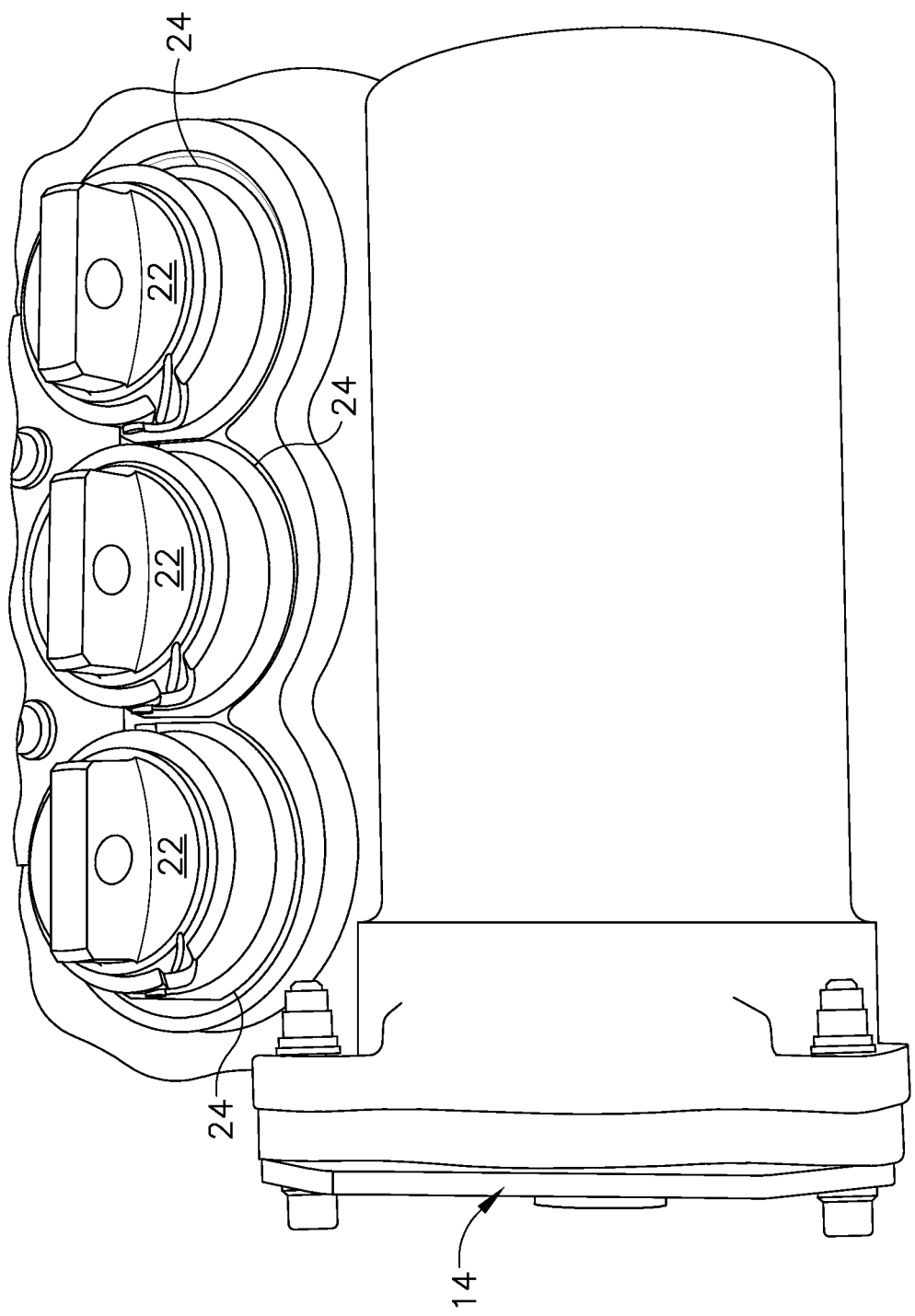
FIG. 2 is a perspective view of an exemplary known pump for use with the lubrication system shown in FIG. 1.

Pump 14 includes a plurality of filters 22 coupled thereto for filtering lubricant being pumped through pump 14. Each filter 22 filters lubricant returned to pump 14 from a corresponding sump 16, 18, and 20 before lubricant from each sump 16, 18, and 20 is merged within pump 14. Each of filters 22 includes a filtering device (not shown) fluidly communicable with a flow of lubricant being returned to pump 14 from the corresponding sump 16, 18, and 20. Although three filters 22 are illustrated, other known lubrication systems may include any number of filters 22. The filtering devices of known lubrication filters 22 may include a variety of devices (not shown) for capturing particles, such as, but not limited to, contaminants and/or other debris. For example, the filtering devices of some known lubrication systems may include, but are not limited to, a magnet and/or a porous sheet of material, such as, but not limited to, a screen, a mesh, and/or a fabric. FIG. 2 is a perspective view of an exemplary known lubrication pump 14 having three known filters 22 coupled thereto for filtering lubricant pumped through pump 14.

Figure 3:
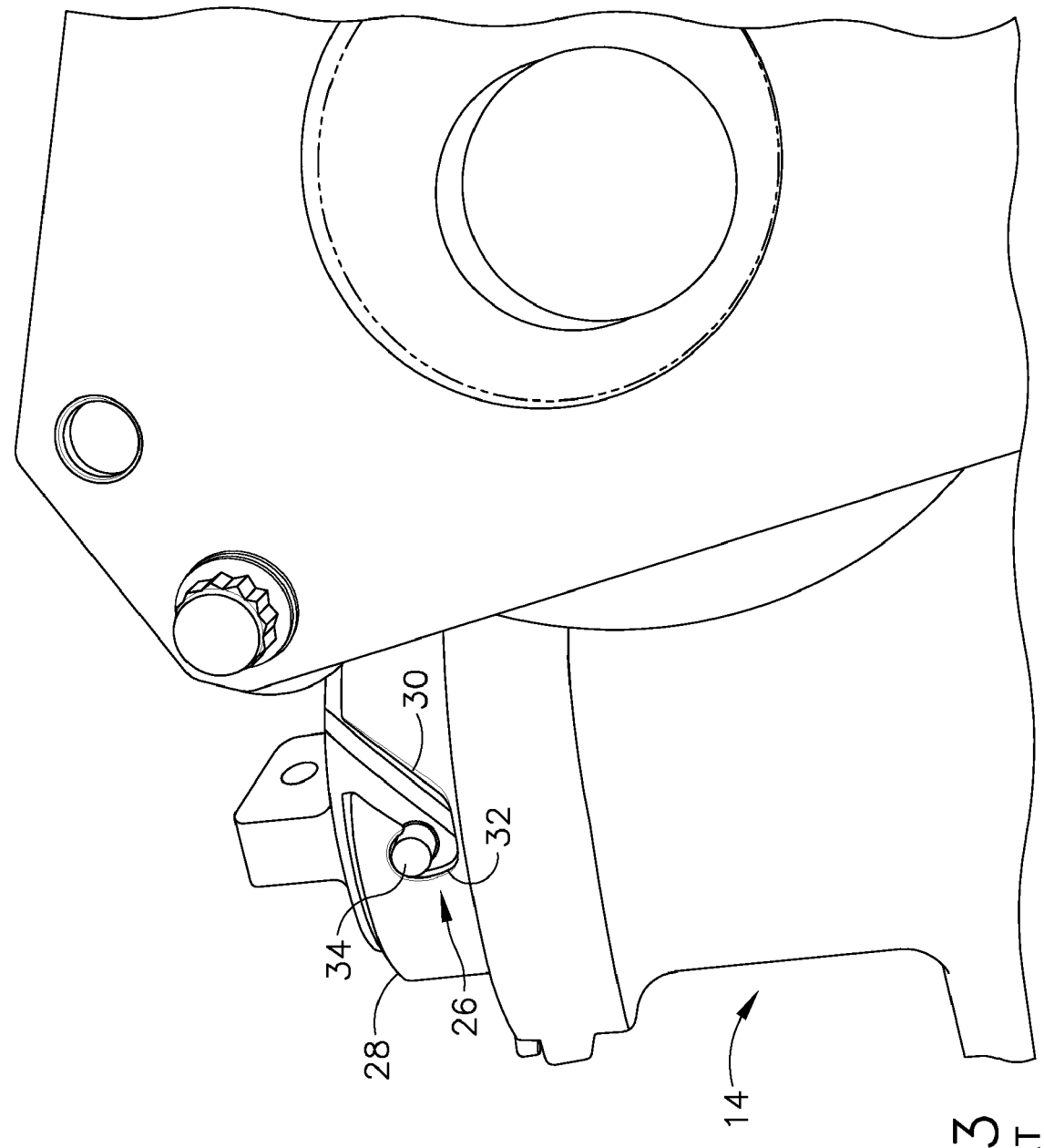
FIG. 3 is a perspective view of a portion of the pump shown in FIG. 2 illustrating an exemplary spring-biased retaining mechanism for coupling a filter to the pump.

Filters 22 may be coupled to pump 14 in a variety of manners, fashions, configurations, arrangements, and/or by a variety of structures and/or means. However, in the exemplary system 10, each filter 22 is received within, and coupled to, a corresponding opening 24 of pump 14 such that each filtering device is fluidly communicable with a flow of lubricant being returned to pump 14 from the corresponding sump 16, 18, and 20. Filters 22 may be coupled to opening 24 by a variety of structures and/or means, such as, but not limited to, a threaded connection and/or a spring-biased retaining mechanism. For example, FIG. 3 is a perspective view of a portion of pump 14 illustrating an exemplary spring-biased retaining mechanism 26 for coupling filters 22 to pump 14. Pump 14 includes an extension 28 extending from pump opening 24 that includes one or more grooves 30 having a retaining portion 32. Filters 22 include one or more extensions 34 that are received within a corresponding groove 30. A spring (not shown) within opening 24 biases extensions 34 into, and retains extensions therein, groove retaining portion 32. As such, the spring facilitates fixedly securing filters 22 to pump 14.

In operation, pump 14 pumps lubricant between sumps 16, 18, and 20 and reservoir 12. More specifically, pump 14 supplies lubricant to sumps 16, 18, and 20 under pressure and the lubricant is returned to pump 14 via the pressure differential across pump 14. Accordingly, pump 14 supplies lubricant to, and scavenges lubricant from, sumps 16, 18, and 20. A corresponding filter 22 of each sump 16, 18, and 20 filters lubricant returned to pump 14 from the corresponding sump 16, 18, and 20 before the lubricant returned from each sump 16, 18, and 20 is merged within pump 14.

Figure 4:
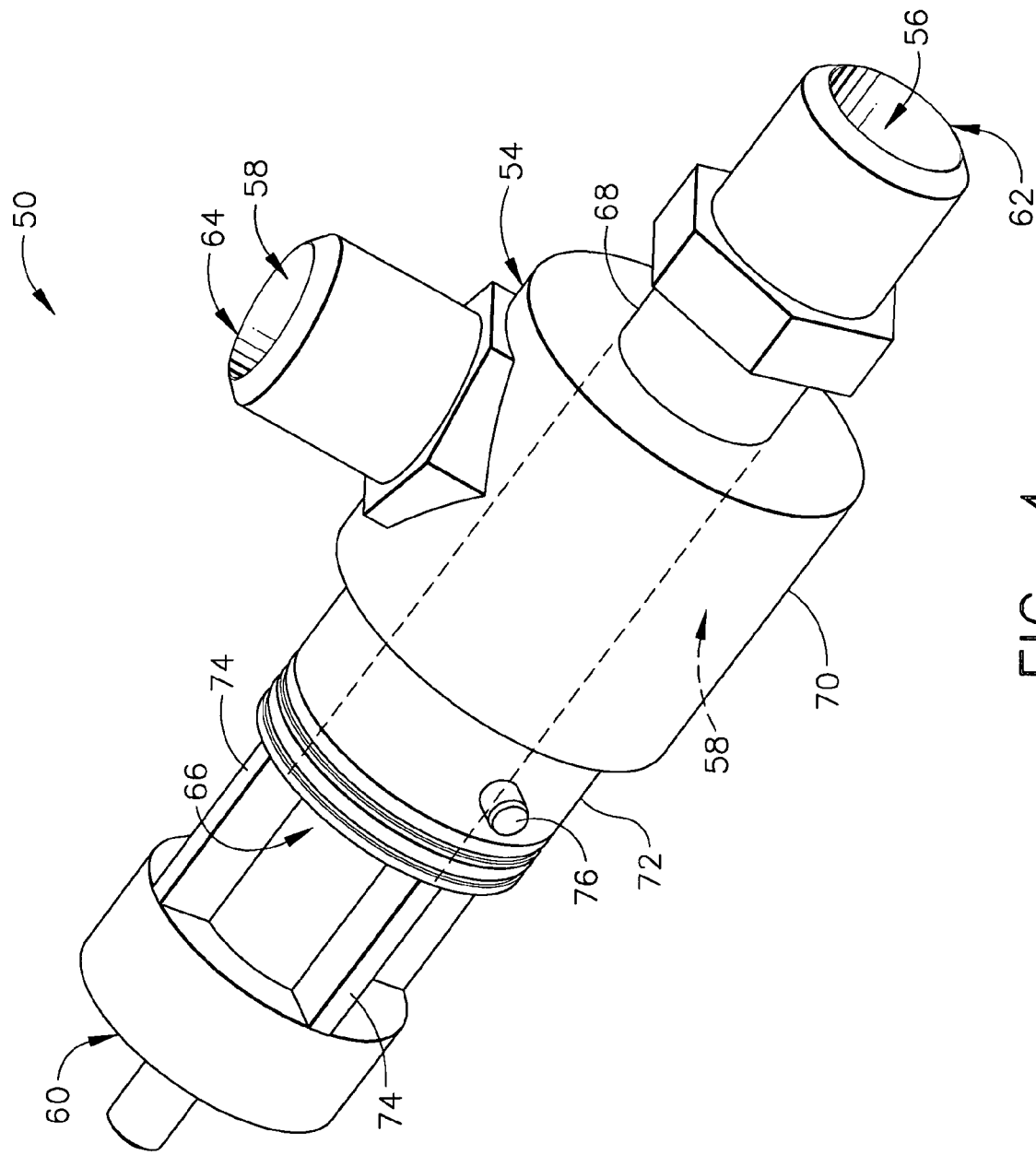
FIG. 4 is a perspective view of an exemplary embodiment of a sampling device for use with the lubrication system shown in FIG. 1.
Figure 5:
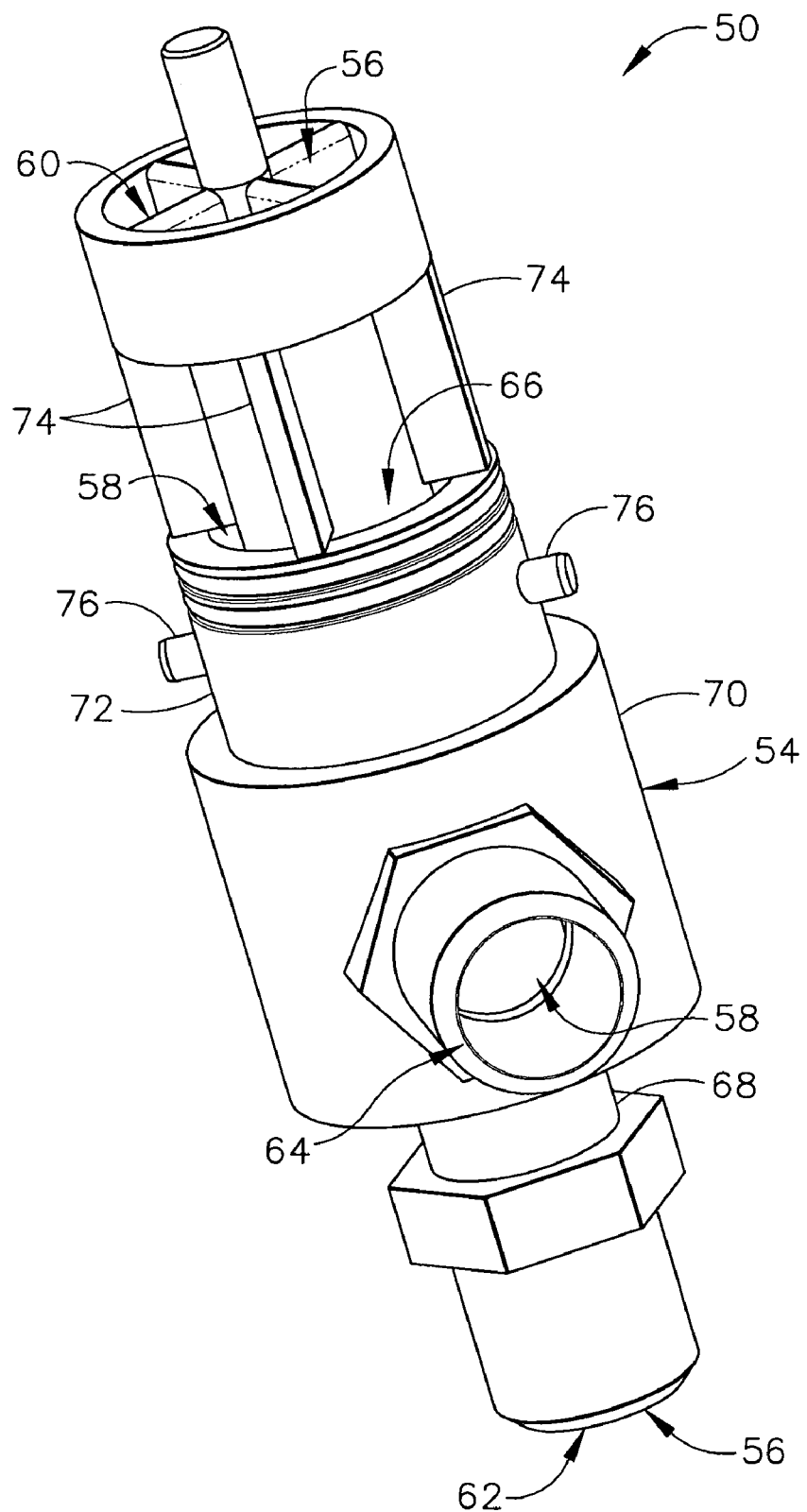
FIG. 5 is another perspective view the sampling device shown in FIG. 4.
Figure 6:
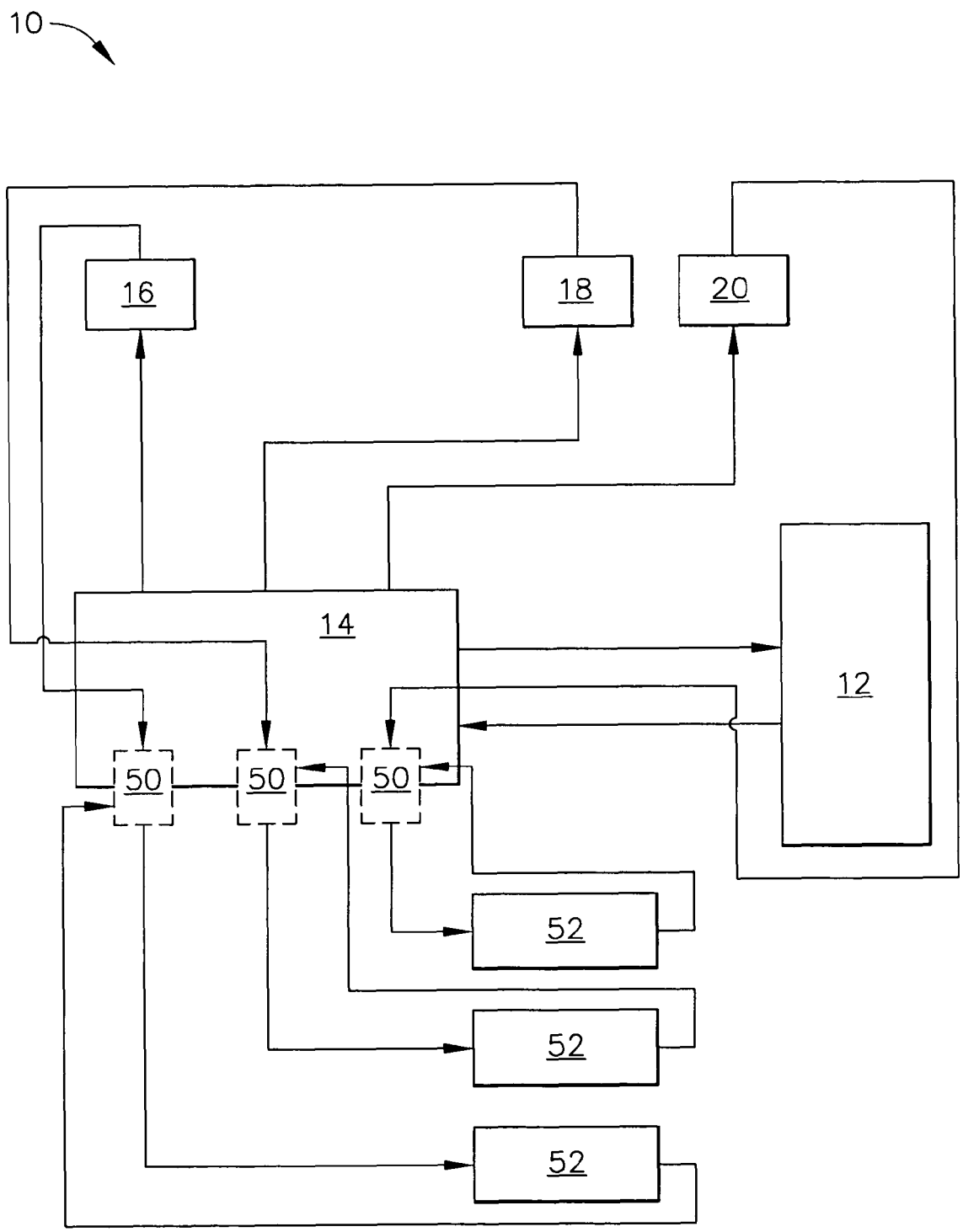
FIG. 6 is a schematic block diagram of the lubrication system shown in FIG. 1 including a plurality of the sampling device shown in FIGS. 4 and 5.

FIGS. 4 and 5 are perspective views of an exemplary embodiment of a sampling device 50 for use with lubrication system 10 (shown in FIG. 1). FIG. 6 is a schematic block diagram of lubrication system 10 having a plurality of sampling devices 50 coupled to pump 14 to replace filters 22 (shown in FIGS. 1-3). Sampling devices 50 each generally discharge fluid returned to pump 14 from a corresponding sump 16, 18, and 20 into a corresponding device 52 external to pump 14. Devices 52 can then each be used to sample lubricant returned from the corresponding sump 16, 18, and 20 to facilitate determining, for example, a source of particles, such as, but not limited to, contaminants and/or other debris, within lubrication system 10. Although three sampling devices 50 are illustrated in FIG. 6, any number of sampling devices 50 may be coupled to pump 14 for sampling fluid from any number of sumps. Moreover, although three devices 52 are illustrated in FIG. 6, any number of devices 52 may be used to sample fluid discharged from any number of sampling devices 50.

Sampling devices 50 each include a body 54 having a fluid passage 56 for discharging lubricant received from a corresponding sump 16, 18, and 20 into a corresponding device 52. Sampling device body 54 also includes a fluid passage 58 for returning sampled lubricant from the corresponding device 52 to pump 14. More specifically, fluid passage 56 includes an inlet 60 coupled in flow communication with pump 14, and more specifically with a flow of lubricant being returned to pump 14 from the corresponding sump 16, 18, and 20. Fluid passage 56 also includes an outlet 62 coupled in flow communication with the corresponding device 52 for discharging lubricant from passage 56 into device 52. Fluid passage 58 includes an inlet 64 coupled in flow communication with the corresponding device 52 for receiving lubricant sampled by device 52. Fluid passage 58 also includes an outlet 66 coupled in flow communication with pump 14 for discharging the sampled lubricant into pump 14. In some embodiments, outlet 62 of fluid passage 56 and/or inlet 64 of fluid passage 58 may be, at least partially, defined by standard line fittings to facilitate fluidly coupling inlet 64 and/or outlet 62 to device 52.

Although an exemplary sampling device 50 is illustrated in FIGS. 4 and 5, sampling device 50 may have any suitable configuration, arrangement, architecture, size, shape, and/or structure that is capable of performing the functions described herein. For example, in the exemplary embodiment, fluid passage 56 is defined by a inner wall 68 of sampling device body 54, and fluid passage 58 is defined by a plurality of outer walls 70 and 72 of body 54. In the exemplary embodiment, outer walls 70 and 72 surround inner wall 68 such that fluid passage 58 surrounds a portion of fluid passage 56. Moreover, walls 68, 70, and 72 are each generally cylindrical and outer walls 70 and 72 are generally concentric with inner wall 68. Furthermore, outlet 66 of fluid passage 58 is, at least partially, defined by a plurality of spaced apart ribs 74. However, and as discussed above, body 54 may have other configurations, arrangements, architectures, sizes, shapes, and/or structures that are capable of performing the functions described herein. For example, sampling device body 54 may have suitable configuration, arrangement, architecture, size, shape, and/or structure that facilitates convenience, manufacturing, and/or installation, and/or that accommodates the configuration, arrangement, architecture, size, shape, and/or structure of a predetermined pump and/or lubrication system.

Figure 7:
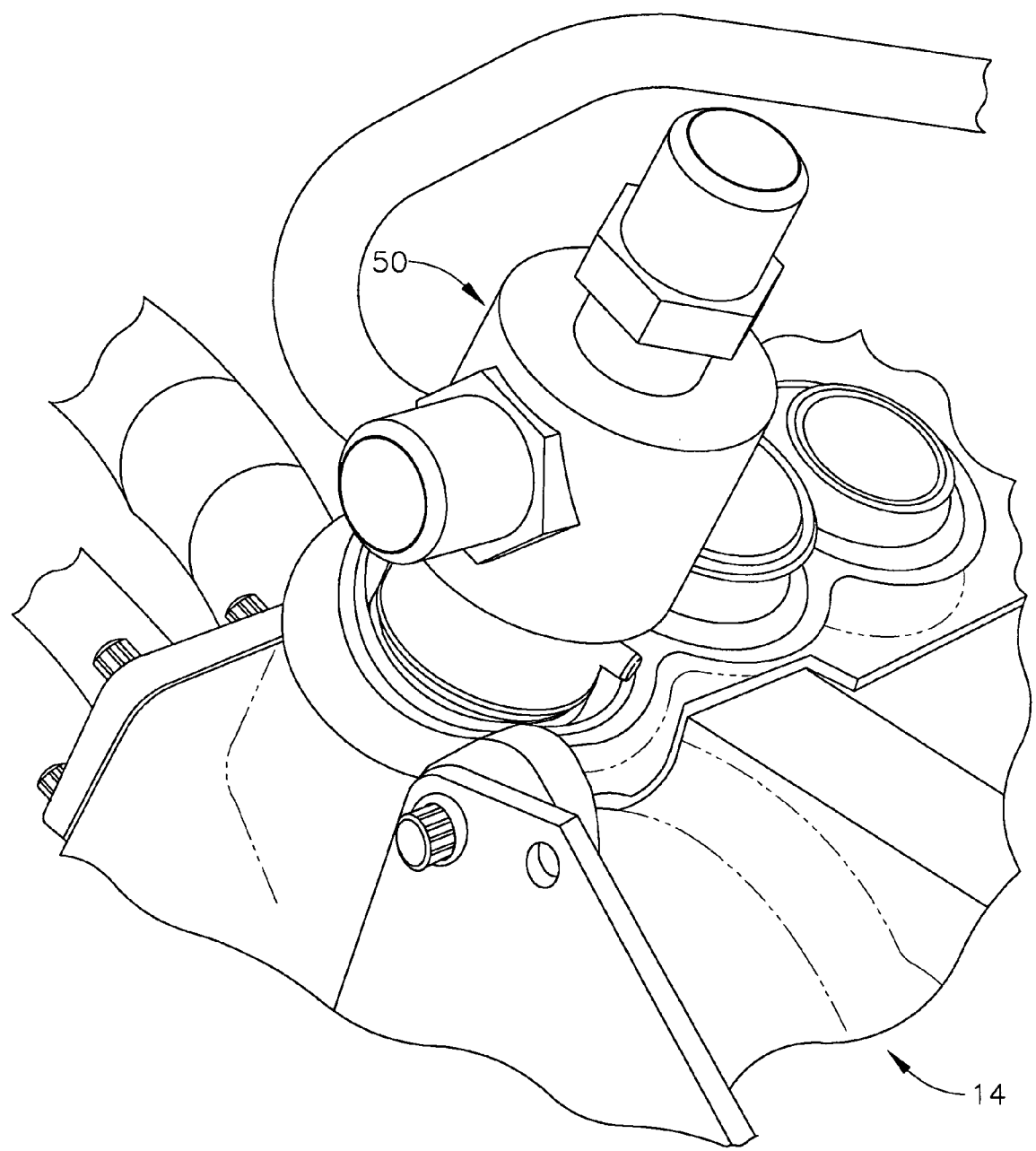
FIG. 7 is a perspective view of a portion of the pump shown in FIG. 2 illustrating an exemplary sampling device coupled thereto.

Sampling devices 50 may be coupled to pump 14 in any suitable manner, fashion, configuration, arrangement, and/or by any suitable structure and/or means that enable sampling devices 50 to perform the functions described herein. In the exemplary embodiment, each sampling device 50 replaces a corresponding filter 22. More specifically, each sampling device 50 is received within, and coupled to, a corresponding opening 24 of pump 14 such that inlet 60 of fluid passage 56 is fluidly communicable with a flow of lubricant being returned to pump 14 from the corresponding sump 16, 18, and 20. Sampling devices 50 may be coupled to opening 24 by any suitable structure and/or means, such as, but not limited to, a threaded connection and/or a spring-biased retaining mechanism. For example, in the exemplary embodiment, sampling devices 50 each include one or more extensions 76 for use with spring-biased retaining mechanism 26 (shown in FIG. 3). FIG. 7 is a perspective view of a portion of an exemplary known lubrication pump 14 illustrating a sampling device 50 coupled thereto. In some embodiments, sampling devices 50 couple to opening 24 in a similar manner, fashion, configuration, arrangement, and/or by similar structure and/or means as a corresponding filter 22 to facilitate interchanging filters 22 and sampling devices 50 on pump 14.

In operation, one or more filters 22 are removed from pump 14 and replaced with a sampling device 50. A flow of lubricant being returned to pump 14 from the corresponding sump 16, 18, and 20 of each sampling device 50 is channeled into fluid passage 56 and discharged into the corresponding device 52, which samples the lubricant. Lubricant sampled by device (s) 52 is channeled into fluid passage 58 and thereby returned to pump 14, wherein it is merged with lubricant from the other sumps 16, 18, and/or 20. Lubricant may be channeled from pump 14 through fluid passage 56, device 52, fluid passage 58, and returned to pump 14, using any suitable means, such as, but not limited to, a pump (not shown) and/or gravity.

Any portion of the gas turbine engine, including any portion of lubrication system 10, may be investigated based on the sampled lubricant. Sampling the lubricant may include determining any property of the lubricant that facilitates investigating the gas turbine engine. The sampled lubricant may be used to investigate, for example, and not limited to, problems, operational characteristics, fatigue, and/or wear of any portion of the gas turbine engine. Based on which sump 16, 18, and 20 the sampled lubricant was scavenged from, the source of the problem, operational characteristic, fatigue, and/or wear may be determined. Accordingly, components of the gas turbine engine, including components of lubrication system 10, can be troubleshot and/or maintained by identifying them as the source of the problem, operational characteristic, fatigue, and/or wear. For example, determining a source of wear and/or fatigue, as well as a severity of such wear and/or fatigue, may facilitate determining an operational life of a component of the gas turbine engine.

Although as discussed above sampling lubricant may include determining any property of the lubricant that facilitates investigating the gas turbine engine, in some embodiments device 52 is a filter that filters lubricant by capturing particles contained within the lubricant, such as, but not limited to contaminants and/or other debris. Based on which sump 16, 18, or 20 the sampled lubricant was scavenged from, a source of the fatigue and/or wear generating such particles may be determined. Device 52 may include any suitable filtering devices for capturing particles, such as, but not limited to, a magnet and/or a porous sheet of material, such as, but not limited to, a screen, a mesh, and/or a fabric. In some embodiments wherein device 52 includes a filter, device 52 is more efficient, defined herein as configured to capture more particles and/or smaller particles, than filters 22. Accordingly, sampling lubricant using sampling device(s) 50 may facilitate obtaining more information about the sampled lubricant, and therefore the gas turbine engine and/or lubrication system 10, than inspecting filters 22. As such, sampling device(s) may facilitate a more efficient investigation of the gas turbine engine and/or lubrication system 10.

Moreover, and although as discussed above sampling lubricant may include determining any property of the lubricant that facilitates investigating the gas turbine engine, in some embodiments device 52 is configured to analyze lubricant, such as, but not limited to, counting particles within the lubricant and/or determining a size of particles within the lubricant. For example, in some embodiments device 52 may count and determine a size of a plurality of differently sized particles within the lubricant. Based on which sump 16, 18, or 20 the sampled lubricant was scavenged from, a source of the fatigue and/or wear generating such particles may be determined. Device 52 may include any suitable devices for analyzing lubricant, such as, but not limited to, an electronic or other type of analyzation device. For example, in some embodiments device 52 is a METALSCAN® brand sensor, available from GASTOPS® Inc. of Pensacola, Fla. In some embodiments wherein device 52 is configured to analyze lubricant, device 52 is more efficient, defined herein as configured to count and/or determine a size of more particles and/or smaller particles, than filters 22. Accordingly, sampling lubricant using sampling device(s) 50 may facilitate obtaining more information about the sampled lubricant, and therefore the gas turbine engine and/or lubrication system 10, than inspecting filters 22. As such, sampling device(s) may facilitate a more efficient investigation of the gas turbine engine and/or lubrication system 10.

Because sampling devices 50 are coupled to pump 14 in place of filters 22 and re-route lubricant to external device 52, the gas turbine engine and/or lubrication system 10 may be investigated without disconnecting lubricant lines from pump 14 and/or reservoir 12. Accordingly, sampling devices 50 may facilitate reducing a cycle time, and therefore possibly a cost, of maintaining the gas turbine engine and/or lubrication system 10. Moreover, sampling devices 50 may facilitate reducing leaks caused by the disconnection of lubricant lines. As discussed above, in some embodiments outlet 62 of fluid passage 56 and/or inlet 64 of fluid passage 58 may be, at least partially, defined by known standard line fittings. Such known standard line fittings may facilitate coupling sampling devices 50 to known standard lines and/or devices 52, which may reduce a cycle time and/or a cost as compared with non-standard lines and/or devices 52.

Although the systems and methods described and/or illustrated herein are described and/or illustrated with respect to a gas turbine engine, and more specifically a gas turbine engine lubrication system, practice of the systems and methods described and/or illustrated herein is not limited to gas turbine lubrication systems, nor gas turbine engines generally. Rather, the systems and methods described and/or illustrated herein are applicable to sampling lubricant from any lubrication system.

Exemplary embodiments of systems and methods are described and/or illustrated herein in detail. The systems and methods are not limited to the specific embodiments described herein, but rather, components of each system, as well as steps of each method, may be utilized independently and separately from other components and steps described herein. Each component, and each method step, can also be used in combination with other components and/or method steps.

When introducing elements/components/etc. of the assemblies and methods described and/or illustrated herein, the articles "a", "an", "the" and "said" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc.

While the invention has been described in terms of various specific embodiments, those skilled in the art will recognize that the invention can be practiced with modification within the spirit and scope of the claims.

What is claimed is:

1. A method for sampling lubricant from a lubrication system including a pump for pumping lubricant between a reservoir and a sump, said method comprising:
   removing a filter from the pump;
   replacing the filter with a sampling device including a first fluid passage and a second fluid passage, the first fluid passage including a first inlet and a first outlet, the second fluid passage including a second inlet oriented orthogonally to the first inlet and a second outlet that extends circumferentially about at least a portion of the first inlet;
   channeling lubricant returned from the sump to the pump into the first fluid passage; and
   discharging lubricant from the pump by discharging lubricant from the first fluid passage.

2. A method in accordance with claim 1 further comprising returning lubricant to the pump by channeling lubricant through the second fluid passage of the sampling device.

3. A method in accordance with claim 1 further comprising sampling lubricant discharged from the first fluid passage.

4. A method in accordance with claim 3 wherein sampling lubricant comprises at least one of filtering lubricant and analyzing lubricant.

5. A method in accordance with claim 4 wherein filtering lubricant comprises filtering lubricant using a filter configured to capture at least one of more particles and smaller particles than the removed filter.

6. A method in accordance with claim 4 wherein analyzing lubricant comprises at least one of counting particles within the lubricant and determining a size of particles within the lubricant.

7. A method in accordance with claim 4 wherein analyzing lubricant comprises analyzing lubricant using a device configured to at least one of count and determine a size of particles of at least one of more particles and smaller particles than the removed filter is capable of filtering.

8. A method in accordance with claim 3 wherein the sampling lubricant discharged from the first fluid passage comprises:
   sampling lubricant for use with a gas turbine engine; and
   investigating the gas turbine engine based on the sampled lubricant.

9. A method in accordance with claim 8 wherein investigating the gas turbine engine based on the sampled lubricant comprises determining a source of at least one of a problem, an operational characteristics, fatigue, and wear based on the sampled lubricant and the sump.

10. A method in accordance with claim 1 wherein replacing the filter with a sampling device comprises at least one of threadably coupling the sampling device to the pump and coupling the sampling device to the pump using a spring-biased retaining mechanism.

11. A method in accordance with claim 3 wherein removing a filter from the pump comprises removing a first filter and a second filter from the pump, wherein replacing the filter with a sampling device comprises replacing the first filter with a first sampling device and replacing the second filter with a second sampling device, wherein channeling lubricant returned from the sump to the pump into the fluid passage comprises channeling lubricant returned from a first sump to the pump into the first sampling device and channeling lubricant returned from a second sump to the pump into the second sampling device, wherein discharging lubricant comprises discharging lubricant from the first sampling device and discharging lubricant from the second sampling device, and wherein sampling lubricant comprises sampling lubricant from the first sump using lubricant discharged from the first sampling device and sampling lubricant from the second sump using lubricant discharged from the second sampling device.

12. A lubrication system comprising:
a pump coupled in flow communication with a sump for pumping lubricant between said pump and said sump;
an external device that is external to said pump, said external device configured to at least one of filter lubricant and analyze lubricant; and
a sampling device coupled to said pump, said sampling device comprising a first fluid passage and a second fluid passage extending circumferentially about said first fluid passage, said first and second fluid passages coupled in flow communication with said pump and with said external device, said first fluid passage configured to receive lubricant returned to said pump from said sump via a first inlet and configured to discharge lubricant into said external device via a first outlet, said second fluid passage configured to receive lubricant from said external device via a second inlet oriented orthogonally to said first inlet and configured to discharge the received lubricant into said pump via a second outlet oriented parallel to said first inlet and said first outlet.

13. A system in accordance with claim 12 further comprising a reservoir for containing lubricant, said pump coupled in flow communication with said reservoir for pumping lubricant between said reservoir and the sump.

14. A system in accordance with claim 12 wherein said second outlet is configured to discharge filtered lubricant therefrom, said second outlet at least partially defined by a plurality of spaced apart ribs.

15. A system in accordance with claim 12 wherein said sampling device is coupled to an opening of said pump that is configured to receive a filter.

16. A system in accordance with claim 15 wherein said external device is configured to at least one of:
capture at least one of more particles and smaller particles than the filter; and
at least one of count and determine a size of particles of at least one of more particles and smaller particles than the filter is capable of filtering.

17. A system in accordance with claim 12 wherein said sampling device is at least one of threadably coupled to said pump and coupled to said pump using a spring-biased retaining mechanism.

18. A system in accordance with claim 12 wherein said system comprises a lubrication system for a gas turbine engine.

19. A system in accordance with claim 18 wherein said sampling device is configured to:
sample lubricant for use with the gas turbine engine; and
investigate the gas turbine engine based on the sampled lubricant.

20. A system in accordance with claim 19 wherein said sampling device is configured to determine a source of at least one of a problem, an operational characteristics, fatigue, and wear based on the sampled lubricant.

* * * * *